United States Patent [19]
Siatkowski

[11] 3,977,082
[45] Aug. 31, 1976

[54] PALATAL EXPANDER

[76] Inventor: Raymond E. Siatkowski, Main St., Essex, Conn. 06426

[22] Filed: Sept. 23, 1975

[21] Appl. No.: 615,922

[52] U.S. Cl. .................................................. 32/14 E
[51] Int. Cl.² ................................................ A61C 7/00
[58] Field of Search ............... 32/14 R, 14 A, 14 E, 32/40 R, 1

[56]         References Cited
         UNITED STATES PATENTS
1,582,570   5/1926   Brust .................................. 32/14 E
3,835,540   9/1974   Beederman ....................... 32/14 E FOREIGN PATENTS OR APPLICATIONS
   11,018   5/1956   Germany ............................ 32/14 E
  668,227   3/1952   United Kingdom ................ 32/14 E
  718,385  11/1954   United Kingdom ................ 32/14 E

*Primary Examiner*—Jack Q. Lever
*Attorney, Agent, or Firm*—McCormick, Paulding & Huber

[57]               ABSTRACT

The expander fits into the upper region of the patient's palatal cavity, and has a longitudinally extending screw which can be given prescribed turns by the patient over a predetermined timetable in order to spread his palate. The screw has forward and rear segments which threadably receive nuts oppositely threaded with respect to one another so that rotation of the screw causes movement of the nuts toward and away from one another. Laterally outwardly movable linkages are pivotally supported on these nuts so that the device operates in the manner of a scissors jack, and orthodontic wires are provided to connect the linkages to orthodontic bands which fit onto the patient's teeth so that the mechanical force and moment achieved in the scissors jack construction can be used to spread the patient's palatine bone segments.

5 Claims, 5 Drawing Figures

PALATAL EXPANDER

BACKGROUND OF THE INVENTION

The present invention relates generally to devices for spreading the human palate, and deals more particularly with a device which fits conveniently well up in the patient's palatal cavity, and which device allows for a relatively high expansion ratio within the anatomical confines of the patient's mouth such that one sized device can be used regardless of the particular individual's palate geometry and palatal expansion needed.

Devices for biasing the upper teeth of a patient, and thereby spreading the palatine bone segments in order to correct orthodontic deformities in the patient's dental structure are well known. Many such deformities can be corrected by spreading the palatine bone segments and allowing spontaneous repositioning of the teeth in conjunction with spreading of the bone segments, whereby to correct these deformities. However, those devices which are available for that purpose are either unduly cumbersonme, or may require removal and replacement in order to achieve the necessary desired palatine expansion.

For example, available orthopedic devices sometimes include a structure involving separate guide pins which not only complicate the assembly steps necessary for such appliances, but also serve to reduce the strength thereof. For instance, the function of such guide pins is to avoid rotary movement of main body sections of the appliance usually resulting from the reacting of adjustments made to these sections is achieving the expanding function. A common form of expansion device is the type having a spindle which is threaded at both ends, but in opposite directions, and which is oriented laterally in the patient's palatal cavity. This configuration of the spindle requires that it be spaced downwardly from the roof of the patient's mouth with the result that it is likely to interfere with normal movement of the tongue, an especially aggravating situation while eating or the like. In such a device, rotation of the spindle causes the two elements to move either toward or away from one another, and associated rods or wires are provided in association with these two elements in order to connect these separable elements with the patient's upper teeth. The two elements, at least initially during the tooth movement process, are spaced relatively close to one another, with the distance increasing as the teeth are separated in response to forces supplied by the appliance on the teeth. When the elements are spaced from each other a distance substantially corresponding to the length of the threaded spindle, the particular expansion device cannot serve any further purpose because of the fact that further expansion of the elements results in the disengagement of the threaded spindle from the elements themselves. Therefore, the patient is required to revisit the orthodontist, and new elements are required to be inserted, or a new spindle, all of which takes time and tends to raise the cost of the treatment process.

Thus, the disadvantages inherent in prior art expansion devices are directly associated with the difficulty and expense involved in interchanging components of these devices during the treatment period. These disadvantages are significant in the palatal expansion treatment process, because advantage must be taken of the biologic phenomenon that two to three weeks are required after a forced system is applied to a tooth for the remodeling mechanisms to occur that result in tooth movement.

The force applied by means of a palatal expansion device is initially dissipated by separation of the palatine bones at the mid-palatal suture if a large enough magnitude of force is applied. This magnitude has been measured to be as high as 35 pounds. If actively applied, or if residual forces remain after three weeks of expansion therapy, the teeth to which the device is attached will tend to move within their bony confines due to the bony remodeling mechanisms. Thus, it will be apparent that a device which need not be removed for replacement of certain of its components will result in an improved treatment process. The palatal expander device disclosed herein makes such an improvement possible.

The lateral width of the disclosed device in its initial (closed) position is much narrower than presently available devices for any given expansion ratio desired. Therefore, the present invention can be initially placed higher in any patient's palatal vault than presently available devices. This higher aspect results in a more favorable moment-to-force ratio (by the law of transmissability of forces) being applied to the teeth, and thereby, during the first three weeks of expansion therapy, to the palatine bones. The more favorable moment-to-force ratio results in more parallel expansion of the palatine bones in the patients' frontal plane. Further, the more favorable moment-to-force ratio is of considerable advantage during the inactive phase of palatal expansion therapy, after the first three weeks of active expansion, when the device is left in position in an inactive holding state for 90 days while allowing bony remodelling at the palatine suture to be completed. The poorer moment-to-force ratios in presently available devices, with the transmitted holding force passing occlusal to the center of resistance of the attached tooth roots, allows the expanded palatine bones to relapse somewhat as the biological bony remodelling mechanism acts about the tooth roots and the teeth move in a tipping manner through the bone as the bone collapses. In attempt to overcome the poorer moment-to-force ratio in order to have more parallel expansion of the palatine bone in the patient's frontal plane and to minimize the common relapse of bony expansion during the inactive holding phase, present devices are sometimes fabricated with molded acrylic contacting the palatal vault tissue. However, the contact of the acrylic with the tissue sometimes results in pressure necrosis of the palatal tissue when present devices are fabricated in this manner, a not surprising finding when it is realized that force levels of up to 35 pounds are involved. The more favorable moment-to-force ratio of the present invention eliminates these problems. The transmitted holding force passes through or apical to the center of resistance of the attached tooth roots. Therefore, any relapsing bony movement would involve pure translation or root movement of the attached teeth, slower and more difficult movements, resulting in less bony relapse of the expanded bony segments during the passive holding phase of therapy.

All presently available devices are activated by inserting a length of wire into the device's lead screw from the anterior end of the mouth and pushing the wire towards the throat to rotate the lead screw. This is an uncomfortable and psychologically stressful movement. The present device, due to its unique construction, is activated by inserting a length of wire into the device's lead screw in the anterior end of the mouth, but pushing the wire laterally right to left, a far more comfortable and less psychological stressful movement.

The unique construction of the present invention allows the user orthodontist to place the device in unilateral cleft palate patients such that unilateral bony expansion of the collapsed bony segment in those patients can be achieved to restore the segments to normal arch form. Presently available devices are incapable of such unilateral action.

SUMMARY OF THE INVENTION

One of the objects of the present invention then is to provide a palatal expander device which when closed fits well into the upper regions of the patient's palatal cavity.

A further object of the present invention is to provide a palatal expander device which need not be removed during the treatment process in order to remove or replace component parts as a result of the spreading action achieved.

A still further object of the present invention is to provide a device which has a relatively high expansion ratio, that is one which will fit well within the anatomical confines of a variety of patients.

A still further object of the present invention is to provide a palatal expander device in which the force achieved increases as the device is expanded. As a result of the unique construction of the device disclosed herein the timetable of turns required for the patient to make in the lead screw of the device follows a readily understandable pattern.

In its presently preferred form the palatal expander device includes a longitudinally extending screw having oppositely threaded segments one of which terminates in a head portion located immediately behind the patient's upper front teeth, and which head portion is adapted to receive a torque applying tool. The front and rear segments of the screw threadably receive oppositely threaded nuts, which nuts in turn pivotally support links, the free ends of which links are in turn joined by an intermediate link so as to provide a structure similar to that of a scissors jack. Each of the intermediate links are adapted to be moved laterally toward and away from the screw in response to rotation of said screw. Orthodontic wire is provided between orthodontic bands on the patient's upper teeth and these intermediate links so as to spread the teeth and hence to also spread the patient's palatine bone segments in a programmed manner such that the above described biologic phenomena can be taken advantage of in carrying out a prescribed orthodontic treatment.

DETAILED DESCRIPTION OF THE PREFERRED EMBODIMENT

Figure 1:
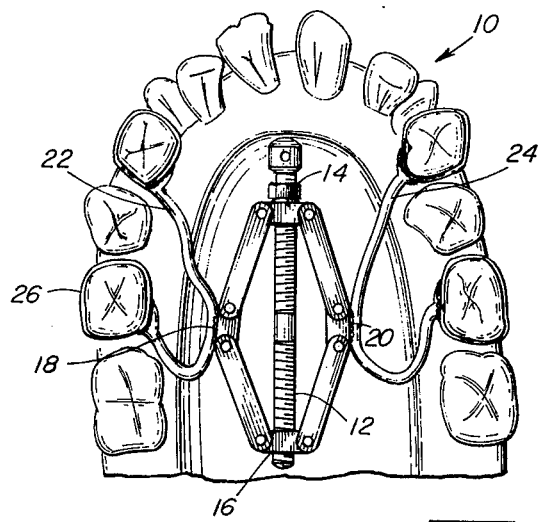
FIG. 1 is a bottom view illustrating the initial placement of the device in the palatal cavity of the patient.

Referring now to the drawing in greater detail, wherein identical reference numerals have been utilized to designate the same or similar parts throughout, and referring first to FIG. 1, an expansion device constructed in accordance with the present invention is illustrated generally at 10, and includes a generally longitudinally extending lead screw 12 rotation of which screw will be accompanied by movement of the nuts 14 and 16 toward one another when the device is used to expand the palate. Left and right hand linkages are provided, and each linkage extends between these nuts, 14 and 16, such that the longitudinal movement of the nuts toward one another will be accompanied by laterally outward movement of the apexes defined by the left and right hand intermediate links 18 and 20. Orthodontic wire elements are attached at their midpoints to the intermediate links 18 and 20 respectively such that the free end portions of these wires 22 and 24 can be attached to bands 26,26 in order to provide a rigid structure for transmitting the lateral forces generated by the expansion device to the teeth of the patient and hence to his palatine bone segments, thereby opening the midpalatal suture in order to take advantage of the biologic phenomena mentioned previously.

Figure 2:
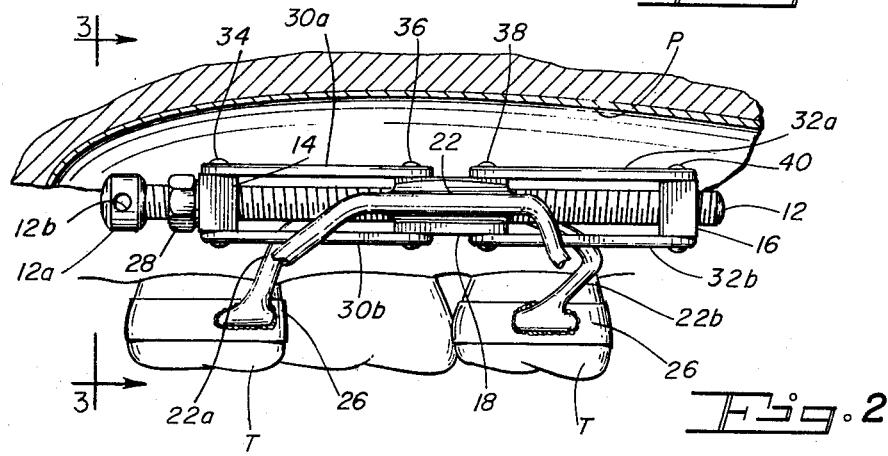
FIG. 2 is a side elevational view with portions broken away or sectioned to illustrate the orientation of the device within the confines of the palatal cavity, two of the teeth on the far side of the patient being there illustrated as connected to the far side of the expander, and the wires on the near side of the expander being broken away.

As best illustrated in FIG. 2, the device in its collapsed configuration can be seen to be well suited to be received in the upper regions of the palatal cavity indicated generally at P, the forward or anterior end of the lead screw 12 having a head portion 12a characterized by radially outwardly extending openings 12b which permit the patient to insert a short length of wire therein in order to achieve the necessary rotation of the lead screw 12 as prescribed by his orthodontist. The two teeth T,T which support the bands 26,26 at the far side of the patient's mouth as illustrated in FIG. 2 are of conventional configuration and need not be described in greater detail herein.

The front and rear nuts 14 and 16 respectively comprise generally rectangular blocks which are threadably received on the associated front and rear oppositely threaded segments of the lead screw 12. As best shown in FIG. 2 a lock nut 28 may be provided adjacent the forward end of the lead screw 12 in order to preclude inadvertant rotation of the lead screw 12.

The intermediate link 18 associated with the left hand side of the expander device is shown in FIG. 2 as being soldered to the orthodontic wire 22 generally at the midpoint thereof. The opposite wire 22 has free end portions 22a and 22b which are soldered to the bands 26,26 mentioned previously. This orthodontic wire is somewhat stronger and less resilient than conventional orthodontic wire in that the forces to be reacted by the structure are somewhat higher in a palatal expander device than is the case with conventional orthodontic devices generally. For example, it has been found that stainless steel wire on the order of 0.05 inches in diameter or greater is presently for the use set forth in this application. In any event the stainless steel wire presently preferred for this orthodontic application should be at least 0.04 inches in diameter and might be as great as 0.06 inches in diameter.

Figure 3:
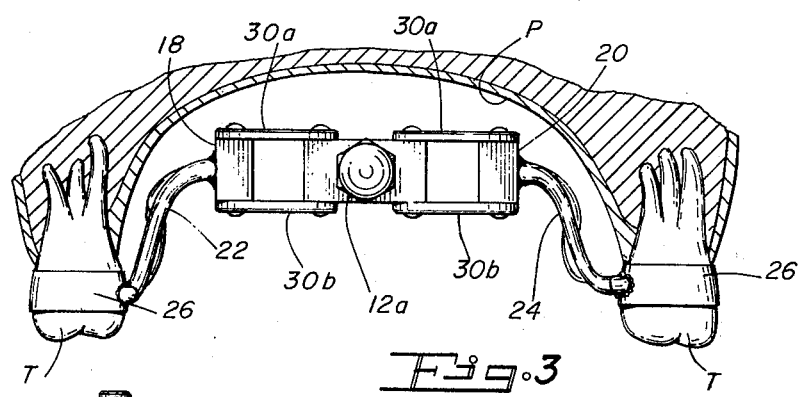
FIG. 3 is a front view taken generally along the line 3—3 of FIG. 2.

Turning next to a more detailed description of the linkages associated with each of the intermediate links 18 and 20 on either side of the orthodontic expander device, FIG. 2 shows the left hand linkage as including a front link means comprising the upper and lower front links 30a and 30b. This front link means 30 is pivotally connected at one end to the front nut 14 by a pivot pin 34, and is pivotally connected at its rear end to the intermediate link 18 by a pivot pin 36. The rear link means comprising the upper and lower links 32a and 32b similarly connected to the intermediate link 18 by a pivot pin 38 and to the rear nut 16 by a fourth pivot pin 40. The right hand linkage comprises a mirror image of the left hand linkage illustrated in FIG. 2, and need not be described in detail. The said right hand linkage structure is illustrated in FIGS. 1 and 3. As so constructed and arranged, the screw 12 can be rotated and the nuts 14 and 16 moved toward one another to drive the intermediate left and right hand links outwardly, thereby exerting an outward or expansion force on the teeth T,T which the orthodontic wires 22 and 24 are clamped.

DETAILED DESCRIPTION OF ALTERNATIVE EMBODIMENT

Figure 4:
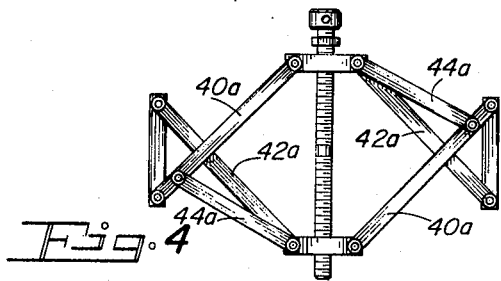
FIG. 4 is a plan view of an alternative version of the expander.
Figure 5:
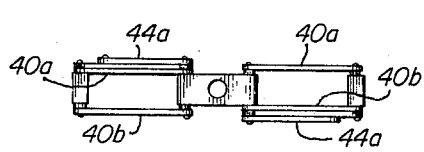
FIG. 5 is a front view of the FIG. 4 expander.

FIG. 4 shows an alternative version wherein identical parts carry reference numerals identical to the FIGS. 1–3 version described above. The scissors link means of FIG. 1 have been replaced by the links 40a, 42a and 44a so that the apex links 18 and 20 will remain parallel to one another as the expander is operated. The left side of the FIG. 4 expander is anti-symmetrical with respect to the right side in that the third or additional link 44a is at the front on the right side and at the rear on the left side.

The front link 40a on the left side corresponds to the rear link 40a on the right side of the FIG. 4 device, and the additional links 44a,44a act between the front and rear nuts 12 and 16 to keep these two links 40a and 40a parallel to one another, hence keeping the apex or outermost links 18 and 20 parallel with one another.

I claim:
1. A device for expanding a patient's palate laterally and comprising in combination:
 a. a longitudinally extending screw having oppositely threaded segments, and having an interior end adapted to be located behind the patient's upper front teeth said interior end defining a head adapted to receive a torque applying tool,
 b. a front nut and a rear nut threadably received on front and rear segments of said screw, said nuts being movable in opposite longitudinal directions in response to rotation of said screw.
 c. left and right hand linkages, each of which linkages are pivotally connected to said front and rear nuts respectively, and each of which linkages includes an apex which moves laterally in response to the longitudinal movement of said nuts, and
 d. orthodontic wires carried by said apexes and including free end portions adapted for attachment to the patient's teeth.

2. The device defined in claim 1 wherein said left and right linkages are mirror images of one another, and wherein each linkage includes a front link means and a rear link means having one end of each link means pivotally connected to said front and rear nuts respectively.

3. The device defined in claim 2 wherein said left and right linkages each further include a short intermediate link member pivotally connected at its opposite ends to said front and rear link means respectively, said intermediate link members defining said laterally movable apexes.

4. The device defined by claim 3 wherein said orthodontic wires are of stainless steel with a diameter in excess of 0.04 inches said wires being so attached to one of said intermediate link members as to provide two free end portions thereof at the left and at the right sides of the device for attachment to at least one of the patient's teeth on each side of his mouth.

5. A device for expanding a patient's palate laterally, and comprising:
 a. a longitudinally extending screw having an interior and adapted to be located behind the patient's upper front teeth and having a head adapted to receive a torque applying tool,
 b. first means threadably received on said screw for longitudinal movement in response to rotation of said screw,
 c. second means rotatably received on said screw,
 d. left and right linkage means pivotally connected to at least one of said first and second means and including left and right apexes which move at least generally laterally in response to said longitudinal movement of said first means, and
 e. orthodontic wires carried by said apexes and including free end portions adapted for attachment to the patient's teeth, via orthodontic bands.

* * * * *